United States Patent [19]

Rainin et al.

[11] Patent Number: 4,779,467
[45] Date of Patent: Oct. 25, 1988

[54] LIQUID-END ASSEMBLY FOR MULTICHANNEL AIR-DISPLACEMENT PIPETTE

[75] Inventors: Kenneth Rainin, Piedmont; Walter S. Watson, San Leandro, both of Calif.

[73] Assignee: Rainin Instrument Co., Inc., Emeryville, Calif.

[21] Appl. No.: 8,217

[22] Filed: Jan. 28, 1987

[51] Int. Cl.⁴ .............................................. B01L 3/02
[52] U.S. Cl. ............................. 73/864.17; 73/863.32; 422/100
[58] Field of Search ........... 73/864.17, 864.18, 864.16, 73/864.14, 864.13, 864.24, 864.25, 864.02, 864.11, 864.01, 863.32; 422/100; 436/180

[56] References Cited

U.S. PATENT DOCUMENTS

| | | | |
|---|---|---|---|
| 3,882,729 | 5/1975 | Roach | 73/864.18 |
| 4,009,611 | 3/1977 | Koffer et al. | 73/864.17 |
| 4,058,370 | 11/1977 | Suovaniemi | 73/864.16 |
| 4,237,095 | 12/1980 | Suovaniemi et al. | 73/864.18 |
| 4,335,621 | 6/1982 | Tervamaki et al. | 73/864.16 |
| 4,459,864 | 7/1984 | Cirincione | 73/863.32 |
| 4,478,094 | 10/1984 | Salomaa et al. | 422/100 |
| 4,591,072 | 5/1986 | Oshikubo | 73/864.18 |
| 4,599,220 | 7/1986 | Yonkers et al. | 73/864.17 |
| 4,616,514 | 10/1986 | Magnussen et al. | 73/864.16 |

FOREIGN PATENT DOCUMENTS

| | | | |
|---|---|---|---|
| 0172508 | 2/1986 | European Pat. Off. | 422/100 |
| 3008347 | 10/1980 | Fed. Rep. of Germany | 422/100 |

*Primary Examiner*—Stewart J. Levy
*Assistant Examiner*—Robert R. Raevis
*Attorney, Agent, or Firm*—Townsend & Townsend

[57] ABSTRACT

A multichannel air-displacement pipette liquid-end assembly having a modular construction, which enables individual components to be easily replaced when they become contaminated or worn. The modular liquid-end assembly also enables selected piston and cylinder components to be selectively removed so that any one of a number of predetermined multichannel pipetting configurations can be employed. Additionally, the modular liquid-end assembly preferably comprises an ejector for providing low-friction mechanical advantage in order to facilitate dislodging spent tips.

8 Claims, 2 Drawing Sheets

U.S. Patent  Oct. 25, 1988  Sheet 1 of 2  4,779,467
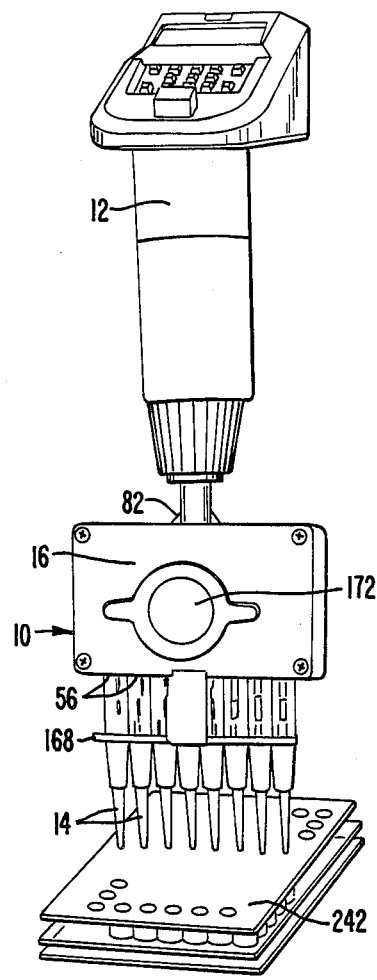
FIG._1.
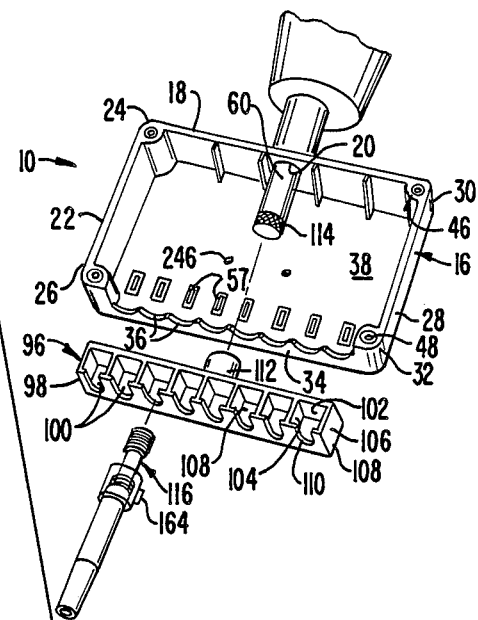
FIG._2.
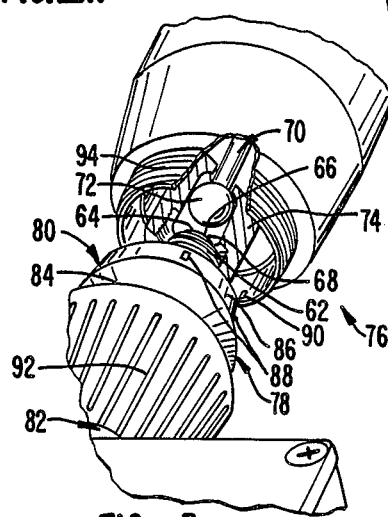
FIG._3.

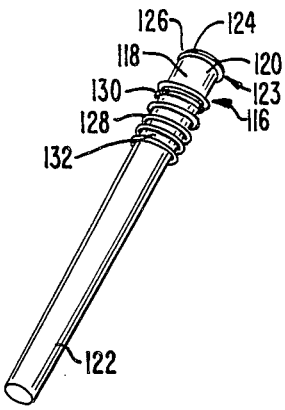
FIG._4.
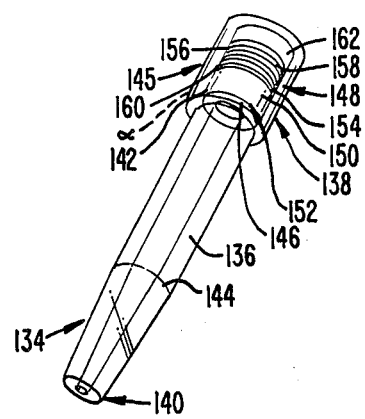
FIG._5.
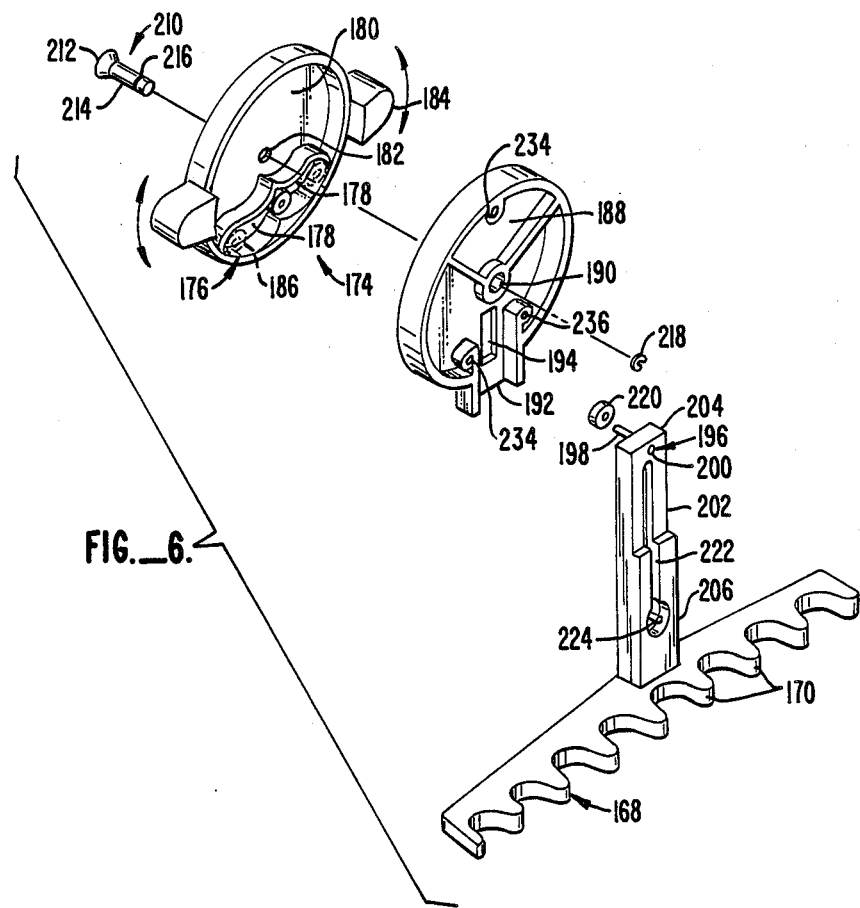
FIG._6.

LIQUID-END ASSEMBLY FOR MULTICHANNEL AIR-DISPLACEMENT PIPETTE

BACKGROUND OF THE INVENTION

This invention relates to pipettes for initially drawing a preselected volume(s) of liquid and subsequently discharging a precise volume(s) of the drawn liquid. More particularly, the invention relates to air-displacement pipettes in which a disposable tip typically contains the drawn liquid, and an air buffer separates the drawn liquid from the piston and cylinder structure typically utilized for drawing and discharging the liquid, so as to prevent contamination of the primary operational elements of the pipette. Specifically, the invention is directed to a multichannel liquid-end assembly for an air-displacement pipette, the liquid-end assembly comprising modular components and further comprising means for facilitating ejection of a spent tip(s).

Various configurations for air-displacement pipettes are known. One known configuration comprises a single barrel, a single piston and cylinder structure within the barrel, a manual or motor-driven linear actuator at one end of the barrel, and a disposable tip at the other end of the barrel. Examples of manually-operated air-displacement pipettes of this type appear in Reed, U S. Pat. No. 3,918,308, and d'Autry, U.S. Pat. No. 3,991,617. Nishi, U.S. Pat. No. 3,915,651, and Magnussen, Jr. et al., U.S. patent application Ser. No. 06/580,587, filed on Feb. 16, 1984, entitled METHODS AND APPARATUS FOR PIPETTING AND/OR TITRATING LIQUIDS USING A HAND HELD SELF-CONTAINED AUTOMATED PIPETTE, and assigned to the same assignee as this application, disclose a motor-driven air-displacement pipette of this type. The referenced manually-operated air-displacement pipettes and the automated pipette disclosed in aforementioned U.S. Ser. No. 06/580,587 further comprise ejection mechanisms typically comprising a manually actuatable sleeve slidable along the exterior surface of the barrel for dislodging a spent tip.

Although the single-channel air-displacement pipettes mentioned above have many uses, in some instances, identical volumes of liquid are sequentially drawn and discharged. The use of a single-channel pipette requires repetitive, time-consuming procedures. Furthermore, in the case of manually-operated pipettes, these repetitive procedures can cause user fatigue and result in imprecise pipetting. Therefore, multichannel configurations for air-displacement pipettes have been developed.

One known multichannel air-displacement pipette is marketed under the registered trademark TITERTEK. The TITERTEK pipette is manufactured by EFLAB OY of Finland and distributed by Flow Laboratories, located in Waltham, Mass. This pipette has a unitary liquid-end assembly comprising a plurality of barrels, a piston and cylinder structure in each barrel, a common actuator connected to each of the pistons, and a tip ejector comprising a thumb-actuatable, spring-returned rake movable along the barrels for dislodging spent tips. One disadvantage of this pipette is that the entire operational mechanism must be replaced if any piston and cylinder is contaminated or worn, since the operational structure is unitary. Another disadvantage is that the user must exert substantial effort when he or she advances the rake against the tips in order to dislodge spent tips from the barrels, since the ejection mechanism does not provide a mechanical advantage.

Another multichannel air-displacement pipette is marketed under the registered trademark CO-STAR, by Co-Star. Inc., located in Cambridge, Mass. As in the case of the TITERTEK pipette, the CO-STAR pipette has a unitary liquid-end assembly with the same disadvantage mentioned above that the entire operational mechanism must be replaced if any piston and cylinder is contaminated or worn. Unlike the TITERTEK pipette, however, the CO-STAR pipette has a tip ejector comprising a spring-returned rake having a top surface in the form of an inclined plane and associated with a finger-actuatable trigger slidable in a track, which moves the wedge-shaped rake downwardly for dislodging spent tips, so that mechanical advantage is applied. However, the rake tends to tilt and bind, which renders the ejection mechanism difficult to operate.

Additionally, disposable tips typically are supplied in trays containing numerous tips. The tips are positioned in the trays such that the distance between adjacent tips corresponds to the distance between adjacent barrels on multichannel air-displacement pipettes, so that the tips can be stabbed onto the barrels. Unfortunately, the unitary liquid-end assemblies of the TITERTEK and CO-STAR pipettes preclude removal of selected barrels so as to be able to stab only so many tips as are desired to be used. Consequently, if less than all channels are desired to be used, the tips must first be stabbed onto the barrels and, thereafter, selectively manually removed or, alternatively, the trays must be specially sorted so that tips are stabbed only onto selected barrels. This is very inconvenient.

It is desirable that a multichannel air-displacement pipette be provided, which enables only contaminated or worn parts to be replaced in lieu of replacing the entire operational mechanism. It is also desirable that a multichannel air-displacement pipette be provided, which enables selected channels to be used without having to remove tips stabbed onto the pipette or, alternatively, having to rearrange pipette tip trays. Furthermore, it is desirable that spent tips be effectively dislodged without excessive difficulty, so that the user is not reconciled to using his or her fingers to assist removal of tips which can often be contaminated with noxious or injurious liquids.

SUMMARY OF THE INVENTION

This invention provides a multichannel air-displacement pipette liquid-end assembly having a modular construction, which enables individual components to be easily replaced when they become contaminated or worn. The modular liquid-end assembly also enables selected piston and cylinder components to be selectively removed so that any one of a number of predetermined multichannel pipetting configurations can be employed. Additionally, the modular liquid-end assembly preferably comprises ejector means for providing low-friction mechanical advantage for dislodging spent tips.

In accordance with one embodiment of the invention, a modular liquid-end assembly is provided for a multichannel air-displacement pipette. This assembly comprises: a housing having a plurality of cylinder ports; means connected to the housing for securing the housing to an external drive module; a shaft mounted in the housing, the shaft being selectively attachable to an actuator contained in the drive module; piston retaining means connected to the shaft and mounted for reciprocal movement in the housing when the housing is connected to the drive module and the drive module is operated, the piston retaining means having a plurality of compartments aligned with the cylinder ports; at least one modular piston means having a first end removably retained in one of the compartments; and at least one modular cylinder means removably retained in an aligned cylinder port, the cylinder means having a first end for receiving a second end of the piston means, the piston means being reciprocated in the cylinder means when the drive module is operated.

The modularity of the construction of the liquid-end assembly in accordance with the invention allows the piston and/or cylinder means to be replaced if there is contamination or wear. Furthermore, selected piston and cylinder means can be removed for varying the multichannel pipetting configuration, so that a number less than all of the channels can be employed for pipetting without first stabbing tips and then removing them by hand or rearranging the tip tray.

Also in accordance with the invention, ejector means is preferably associated with the modular liquid-end assembly for dislodging at least one removably attachable tip frictionally mounted at a proximal end to a second end of the cylinder means, a distal end of the tip for containing liquid drawn into and later discharged from the tip when the drive module is operated. The ejector means comprises: a movable contact member disposed tangent to the cylinder means; cam means comprising at least one guide and further comprising roller means movable in the guide; and a rotary handle connected to the guide for actuating the cam means from a home position to an eject position; the movable contact member being connected to the roller means; whereby actuation of the rotary handle causes the roller means to move along the guide for imparting movement to the movable contact member for dislodging the tip.

The ejector means provides sufficient mechanical advantage for effectively dislodging spent tips. This assures removal of the spent tips so that the user is not reconciled to remove tips with his or her fingers.

BRIEF DESCRIPTION OF THE DRAWINGS

The above and other features of the invention and the concomitant advantages will be better understood and appreciated by those skilled in the art in view of the description of the preferred embodiments given below in conjunction with the accompanying drawings. In the drawings:

FIG. 1 is an isometric view of one embodiment of modular multichannel liquid-end assembly in accordance with the invention attached to an external drive module and having a plurality of attached disposable tips positioned for discharging multiple samples of liquid;

FIG. 2 is a exploded view of the liquid-end assembly shown in FIG. 1;

FIG. 3 is an isometric view which illustrates a detail of the liquid-end assembly shown in FIG. 1 for attachment to the drive module;

FIG. 4 is an isometric view of a modular piston assembly included in the liquid-end assembly shown in FIG. 1;

FIG. 5 is an isometric view of a modular cylinder assembly included in the liquid-end assembly shown in FIG. 1: and FIG. 6 is an exploded view of an embodiment of tip ejector preferably associated with the liquid-end assembly shown in FIG. 1.

DETAILED DESCRIPTION OF THE PREFERRED EMBODIMENTS

Referring to the drawings, FIG. 1 shows an embodiment of a modular multichannel liquid-end assembly in accordance with the invention, generally indicated by the numeral 10. The liquid-end assembly 10 is shown connected to an external drive module 12. The drive module 12, for example, can be a hand-held, motor-driven, automated drive module, such as the drive module marketed by Rainin Instrument Co. Inc., of Woburn, Mass., under the trademark EDP-M8. A plurality of disposable tips 14 is shown attached to the liquid-end assembly 10. The tips 14, for example, can be disposable tips marketed by Rainin Instrument Co. under the trademark CLEAN-PAK II.

As shown in FIGS. 1 and 2, the liquid-end assembly 10 comprises a housing 16. The housing 16 preferably comprises a top wall 18 having an aperture 20. The aperture 20 is preferably centrally located along the top wall 18.

The housing 16 also comprises a first side wall 22 having a top 24 and a bottom 26. The housing 16 further comprises a second side wall 28. The second side wall 28 has a top 30 and a bottom 32. The top 24 of the first side wall 22 and the top 30 of the second side wall 28 are respectively connected to opposite ends of the top wall 18, as shown in FIG. 2.

The housing 16 also comprises a bottom wall 34. The bottom wall 34 has a plurality of first approximately semicircular cutouts 36 along the length of the bottom wall. The bottom 26 of the first side wall 22 and the bottom 32 of the second side wall 28 are respectively connected to opposite ends of the bottom wall 34, as shown in FIG. 2.

The housing 16 further comprises a rear wall 38. The rear wall 38 is connected along the rear edges of the top wall 18, first side wall 22, second side wall 28, and bottom wall 34.

Finally, the housing 16 comprises a front wall 40. The front wall 40 has a bottom lip 42. The bottom lip 42 has a plurality of second approximately semicircular cutouts 44 along the length of the bottom lip.

The front wall 40 is preferably removably attachable along the front edges of the top wall 18, first side wall 22, second side wall 28, and bottom wall 34 as follows. Wells 46 are provided at the location of the corners where the top wall 18, first side wall 22, second side wall 28, bottom wall 34, and rear wall 38 intersect. Threaded inserts 48 are seated in the wells 46. Holes 50 are provided in the corners of the front wall 40. The front wall 40 preferably includes ribs 52 for facilitating alignment of the holes 50 with the inserts 48. Screws 54 are inserted through the holes 50 and threadedly engaged in the inserts 48 for removably attaching the front wall 40 to the remainder of the housing 16.

Preferably, the top wall 18, first side wall 22, second side wall 28, bottom wall 34, and rear wall 38 comprise a single molded plastic structure. Similarly, the front wall 40 preferably comprises a molded plastic structure.

When the front wall 40 is attached to the remainder of the housing 16, the first cutouts 36 are positioned opposite the second cutouts 44 so as to define cylinder ports 56, as shown in FIG. 1. Preferably, as shown in FIG. 2, sockets 57 are formed on the surface of the rear wall 38 interior of the housing 16 for retaining structure within the cylinder ports 56, as will be described in greater detail later. Also, bosses 58 are formed on the surface of the front wall 40 interior of the housing 16 in order to aid positioning of the structure within the cylinder ports 56, as will be described in greater detail later.

The liquid-end assembly 10 also comprises a shaft 60. The shaft 60 extends through the aperture 20.

The shaft 60 is preferably attached to the drive module 12 as follows. As shown in FIG. 3. the shaft 60 has a first end 62 having a threaded circumference. Preferably, a pedestal 64 is provided. The pedestal 64 has a bottom 66 connected to the first end 62 of the shaft 60. The pedestal 64 also has a concave top 68.

The external drive module 12 preferably comprises a linear actuator 70. The linear actuator 70 preferably has an aligning sphere 72 threadedly engaged to the end of the linear actuator. The sphere 72 meshes with the concave top 68 of the pedestal 64 for aligning the linear actuator 70 with the shaft 60.

Furthermore, the sphere 72 retains a connecting nut 74 slidable along the linear actuator 70. When the sphere 72 is meshed with the concave top 68 of the pedestal 64, the connecting nut 74 is threadedly engaged with the first end 62 of the shaft 60 for interconnecting the shaft with the linear actuator 70. Preferably, when the connecting nut 74 is tightened on the first end 62 of the shaft 60, the sphere 72 can slightly retract away from the concave top 68 of the pedestal 64, thereby creating a control clearance between the sphere and the pedestal.

The liquid-end assembly 10 further comprises means 76 connected to the housing 16 for securing the housing to the drive module 12. As shown in FIG. 3, the means 76 comprises an extension 78 projecting away from the top wall 18. The extension 78 comprises an approximately frustoconical member 80 having a tapered bore aligned with the aperture 20 through which the shaft 60 extends into the housing 16. The extension 78 has a first end 82 connected to the top wall 18. The extension 78 has a second end 84 with a flange 86. The flange 86 preferably has a plurality of slots 88. The drive module 12 is preferably provided with at least one tab 90. One of the slots 88 interfits with the tab 90 when the extension 78 is moved into contact with the drive module 12. The slots 88 and the tab 90 are preferably arranged for permitting the liquid-end assembly 10 to be positioned with respect to the drive module 12, as shown in FIG. 1, or, alternatively, rotated 90°, 180°, or 270° with respect to the position shown in FIG. 1.

Additionally. the means 76 comprises an interiorly threaded collar 92 surrounding the extension 78. The drive module 12 is provided with a threaded neck 94. When one of the slots 88 is interfitted with the tab 90, the collar 92 is threadedly engaged with the neck 94 for securing the liquid-end assembly 10 to the drive module 12. Since, the shaft 60 is connected to the linear actuator 70 by means of the connecting nut 74, the shaft is reciprocated when the housing 16 is connected to the drive module 12 by the means 76 and the drive module is operated.

Referring again to FIG. 2, the liquid-end assembly 10 also comprises piston retaining means 96. The piston retaining means 96 comprises a rack 98 having a plurality of cells 100. Each of the cells 100 comprises a top wall 102, a first side wall 104, a second side wall 106, a rear wall 108, and a U-shaped bottom wall 110. The piston retaining means 96 further comprises a cylindrical projection 112. Preferably, the shaft 60 has a second end 114 with a knurled circumference. The second end 114 of the shaft 60 is inserted into the cylindrical projection 112 for connecting the shaft 60 to the piston retaining means 96 so that the piston retaining means reciprocates in the housing 16 when the shaft is reciprocated by the drive module 12.

The liquid-end assembly 10 further comprises modular piston means 116. As shown in FIG. 4, the piston means 116 comprises a cylindrical rod 118. The rod 118 has a first end 120 and a second end 122. The piston means 116 further comprises spring capturing means 123 disposed proximate the first end 120 of the rod 118. The spring capturing means 123 preferably comprises a circumferential groove 124 disposed proximate the first end 120 of the rod 118. The spring capturing means 123 also preferably comprises a clip 126 disposed in the groove 124. Finally. the piston means 116 comprises a piston spring 128. The piston spring 128 has an upper end 130 and a lower end 132. The piston spring 128 is disposed about the rod 118 between the second end 122 of the rod and the clip 126.

The piston retaining means 96 retains the piston means 116 as follows. One of the cells 100 of the piston retaining means 96 holds the piston means 116 so that the first end 120 of the rod 118 abuts the top wall 102 of the cell and the piston spring 128 is compressed within the cell with the upper end 130 of the piston spring contacting the clip 126 and the lower end 132 of the piston spring contacting the U-shaped bottom wall 110 of the cell, the second end 122 of the rod extending through the U-shaped bottom wall, as shown in FIG. 2. The upper end 130 and the lower end 132 of the piston spring 128 are preferably flattened for increasing frictional contact between the upper end of the piston spring and the clip 126, as well as between the lower end of the piston spring and the U-shaped bottom wall 110 of the cell 100.

The liquid-end assembly 10 also comprises modular cylinder means 134. The cylinder means 134 comprises a cylindrical member 136. The cylindrical member 136 has a first end 138 receiving the second end 122 of the rod 118 of the piston means 116. The cylindrical member 136 also has a second end 140 tapered for receiving one of the disposable tips 14. The cylindrical member 136 further comprises a ledge 142 interior of the cylindrical member and located proximate the first end 138 of the cylindrical member. Preferably, the ledge 142 slopes downwardly so as to define an angle α between the inside surface of the cylindrical member 136 and the upper surface of the ledge, which is preferably 120°. The cylindrical member 136 also comprises a shoulder 144 interior of the cylindrical member and located proximate the second end 140 of the cylindrical member, against which the rod 118 abuts when the piston means 116 completes a discharge stroke.

The cylinder means 134 also comprises sealing means 145. The sealing means 145 preferably comprises an O-ring seal 146 residing on the ledge 142. Silicone grease, for example, is preferably applied to the O-ring seal 146 in order to increase the seal and reduce frictional drag between the rod 118 and the O-ring seal. The sealing means 145 further comprises seal compression means 148 disposed interior of the cylindrical member 136 proximate the first end 138 of the cylindrical member.

The seal compression means 148 preferably comprises a tubular element 150. The tubular element 150 has a first end 152 and a second end 154. The first end 152 of the tubular element 150 abuts the O-ring seal 146. The seal compression means 148 also comprises a coil spring 156. The coil spring 156 has an upper end 158 and a lower end 160. The lower end 160 of the coil spring 156 abuts the second end 154 of the tubular element 150. Finally, the seal compression means 148 comprises a ring 162 affixed to the first end 138 of the cylindrical member 136 so that the upper end 158 of the coil spring 156 abuts the ring. The rod 118 of the piston means 116 extends through the seal compression means 148 comprising the tubular element 150, coil spring 156, and ring 162. The ring 162 secures the O-ring seal 146, tubular element 150, and coil spring 156 within the cylindrical member 136 with the upper end 158 of the coil spring contacting the ring and the lower end 160 of the coil spring contacting the second end 154 of the tubular element such that the first end 152 of the tubular element is urged against the O-ring seal for compressing the O-ring seal against the ledge 142, as well as expanding the O-ring seal radially inwardly against the rod 118 of the piston means 116, so that the O-ring seal seals against the ledge and the piston means. The cylindrical member 136 and the ring 162 can be constructed from plastic material, and the ring can be ultrasonically welded to the first end 138 of the cylindrical member.

The cylinder means 134 is installed in one of the cylinder ports 56 as follows. A detent 164 formed on the first end 138 of the cylindrical member 136 projects radially outwardly from the cylindrical member. The detent 164 is inserted in one of the sockets 57 formed on the rear wall 38 of the housing 16 for retaining the cylinder means 134 in the cylinder ports 56. Additionally, a pair of the bosses 58 formed on the front wall 40 interior of the housing 16 extend toward the cylinder means 134 and contact the cylindrical member 136 when the cylinder means is installed in the cylinder ports 56 for positioning the cylinder means in the cylinder ports when the front wall 40 is attached.

The liquid-end assembly 10 also comprises ejector means 166 mounted on the housing 16 for dislodging spent tips 14. The ejector means 166 comprises a movable contact member 168. The movable contact member 168 preferably comprises a plurality of teeth 170 aligned with the cylinder ports 56 with the teeth being disposed between the cylinder ports and the tips 14.

The ejector means 166 also comprises operator means 172 for selectively advancing the teeth 170 of the movable contact member 168 against the tips 14 for dislodging the tips. As shown in FIG. 6, the operator means 172 comprises cam means 174. The cam means 174 comprises a guide 176. The guide 176 preferably has two opposed lobes 178. The guide 176 is preferably formed in a first cap 180. The first cap 180 has a central bore 182. The cam means 174 also comprises a handle 184 connected to the guide 176 for actuating the cam means from a home position, wherein the handle 184 is turned about 90 degrees from the position shown in FIG. 6, to an eject position, as shown in FIG. 6. The handle 184 is preferably formed as outward projections of the periphery of the first cap 180.

The cam means 174 also comprises roller means 186 movable in the guide 176. The roller means 186 preferably comprises a low-friction roller ball bearing which enables efficient cam action.

The cam means 174 further comprises a second cap 188. The second cap 188 has a central bore 190, as well as a channel 192 with a window 194. The second cap 188 overlies the first cap 180 with the central bore 182 of the first cap aligned with the central bore 190 of the second cap so as to capture the roller means 186 in the guide 176.

The cam means 174 also comprises a peg 196. The peg 196 has a first end 198 that extends through the window 194 and is disposed in the roller means 186. The peg 196 also has a second end 200.

The cam means 174 further comprises a bar 202. The bar 202 has a first end 204 connected to the second end 200 of the peg 196. The bar 202 has a second end 206 connected to the movable contact member 168.

The ejector means 166 is preferably mounted on the housing 16 as follows. The front wall 40 of the housing 16 preferably has an opening 208. An axle 210 has an enlarged head 212 and a body 214 having a circumferential groove 216. The body 214 of the axle 210 is inserted through the aligned central bores 182 and 190. A clip 218 is disposed in the circumferential groove 216. The bar 202 is sandwiched between the channel 192 and the front wall 40 of the housing 16 and constrained to slide in the channel 192 when the peg 196 is moved upwardly and downwardly in the window 194 as the roller means 186 moves along one of the lobes 178 of the guide 176 when the handle 184 is rotated. Since there are preferably two lobes 178, cam action is provided whether the handle 184 is rotated clockwise or counterclockwise. In one specific implementation, the movable contact member 168 travels linearly 0.004 inch for every degree of rotation of the handle 184. In a contemplated modification of the ejector means 166, the peg 196 can have a diameter smaller than the inside diameter of the roller means 186 and a washer 220 can be placed around the peg and roll along the side edges of the window 194 so as to prevent the peg from binding in the window.

Wells 234 are preferably formed on the interior surface of the second cap 188. Threaded inserts 236 are seated in the wells 234. Holes 238 are provided in the front wall 40 of the housing 16. Fasteners 240, which can comprise additional screws 54, are inserted through the holes 238 in the front wall 40 and threadedly engaged in the inserts 236 for mounting the ejector means 166 on the housing 16.

A plurality of the fasteners 240 preferably has an integral threaded standoff 244. Holes 246 are additionally provided in the rear wall 38. The holes 246 align with the standoffs 244 when the front wall 40 is connected to the remainder of the housing 16. Additional screws 54 are threadedly engaged with the standoffs 244 for more rigidly securing the front wall 40 to the remainder of the housing 16.

The ejector means 166 also preferably comprises an elongated trough 222 having a first post 224 formed at one end. Additionally, a second post 226 is formed on the surface of the front wall 40 exterior to the housing 16. An extension spring 228 is also provided. The extension spring 228 has a first end 230 connected to the first post 224 and a second end 232 connected to the second post 226 for returning the cam means 174 to the home position shown in solid lines in FIG. 6.

In operation, the front wall 40 of the housing 16 can be detached by removing the screws 54. After the front wall 40 is detached, the multichannel pipetting configuration for the liquid-end assembly 10 can be selected by locating modular piston means 116 in appropriate cells 100 and corresponding modular cylinder means 134 in cylinder ports 56. The front wall 40 is then reattached and held in place by replacing the screws 54.

The liquid-end assembly 10 can then be attached to the drive module 12 by seating the sphere 72 on the pedestal 64 and rotating the connecting nut 74 into engagement with the shaft 60. Then, the collar 92 is rotated onto the neck 94 to complete mounting the liquid-end assembly 10 to the drive module 12.

The drive module 12 and connected liquid-end assembly 10 are then positioned over a tray containing the tips 14. One of the tips 14 is stabbed onto the second end 140 of the cylindrical member 136 of each of the cylinder means 134 extending through the cylinder ports 56.

The drive module 12 and the liquid-end assembly 10 with the attached tips 14 are then transported to a liquid reservoir, the tips are lowered into the liquid, and the drive module is operated for retracting the linear actuator 70 which, in turn, retracts the shaft 60 and the rod 118 of each of the piston means 116 within each of the corresponding cylinder means 134. This draws liquid into each of the attached tips 14.

Thereafter, the drive module 12, together with the liquid-end assembly 10 and attached tips 14 containing the drawn liquid, are transported to a liquid discharge station, as shown in FIG. 1, and the drive module is operated to extend the linear actuator 70, shaft 60, and rod 118 of each of the piston means 116 into the associated cylinder means 134 for discharging the liquid into a multi-compartmented receptacle 242. Liquid discharge is completed when the rod 118 of each of the piston means 116 bottoms on the shoulder 144.

The tips 14 are now contaminated by the liquid. The contaminated tips 14 can be ejected by grasping the handle 184 and rotating the handle in either a clockwise or counterclockwise direction. Rotation of the handle 184 actuates the cam means 174, which imparts linear movement to the movable contact member 168 so that the teeth 170 contact the tips 14 and dislodge them from the cylindrical member 136 of each of the cylinder means 134. New tips 14 can then be stabbed onto the cylindrical members 136.

The foregoing description is offered primarily for purposes of illustration. Various modifications are contemplated. In one modification, the shaft 60 can be threaded along a greater portion of its length, and the linear actuator 70 can be replaced by a rotary actuator in the form of a nut threadedly engaged with the shaft, a releasable connection being provided between the second end 114 of the shaft and the piston retaining means 96. Alternatively, the second end 114 of the shaft can be threaded, and the linear actuator 70 can be a rotary actuator, the cylindrical projection 112 being in the form of a nut. Also, the slots 88 and the tab 90 can be eliminated so that the liquid-end assembly 10 can be oriented at any rotational position with respect to the drive module 12. Furthermore, an enlarged head on the rod 118 can be substituted for the groove 124 and the clip 126. Also, the O-ring seal 146 and the seal compression means 148 can be replaced by an expandable ring seal manufactured by Bal Seal, located in Santa Ana, Calif., or by a dry seal such as disclosed in aforementioned U.S. Ser. No. 06/580,587, for example. Furthermore, the movable contact member 168 can simply assume the form of a plate with holes, through which the cylindrical members 136 extend, or a bar tangent to the cylindrical members. While a variety of embodiments has been disclosed, it will be readily apparent to those skilled in the art that numerous other modifications and variations not mentioned above can still be made without departing from the spirit and scope of the invention as claimed below.

What is claimed is:

1. A liquid-end assembly for a multichannel pipette, the liquid-end assembly comprising:

a housing having an opening in a top wall for receiving a shaft connectable to a drive mechanism of the pipette for axial movement in the housing;

a plurality of cylinders each with a lower open end extending from a bottom wall of the housing to releasably receive a removable pipette tip;

a plurality of pistons each mounted for axial movement in and through an open upper end of a different cylinder in response to axial movement of the shaft in the housing; and an ejector for dislodging the removable pipette tips from the lower ends of the cylinders, the ejector comprising:

a slide mounted for vertical reciprocating movement in a channel carried by a front wall of the housing and carrying a tip ejecting member above the tips for engaging and dislodging the tips upon downward movement of the member relative to the tips, and hand operable slide actuating means for imparting vertical reciprocating movement to the slide including a handle supported for hand turning relative to the housing on an axis substantially normal to the direction of reciprocating movement of the slide, a guide cam carried by the handle for turning therewith and a roller secured to the slide for rolling on and following the guide cam with a hand turning of the handle such that a turning of the handle produces vertical movement of the slide and tip ejecting member.

2. The liquid-end assembly of claim 1 further including a return spring coupled to the slide to automatically return the slide to an upward home position following downward movement to eject removable pipette tips, and a release of the handle.

3. The liquid-end assembly of claim 2 wherein the guide cam of the ejector includes two opposed and connected lobes extending laterally on opposite sides of the vertical ejector slide to guide the roller and drive the slide and the tip ejecting member in a downward direction to eject the removable pipette tips in response to either a clockwise or a counterclockwise turning of the handle from a home position for the handle.

4. The liquid-end assembly of claim 3 wherein:

the guide cam is carried on a back face of a hand-turnable cap having a central opening for receiving an axle extending from a front face of the housing above the roller, the guide cam is carried by the back face of the cap between the roller and the axle to extend on opposite sides of the slide, and the handle is defined by outward projections from the cap.

5. The liquid-end assembly of claim 1 wherein the assembly is modular, the cylinders and pistons are readily replaceable as components in removable piston and cylinder modules as hereinafter defined, the assembly is releasably attachable to the drive mechanism of the pipette, and the housing is closed having a manually openable front wall carrying the ejector and a pluraltiy of cylinder ports in a bottom wall, and the assembly further includes:

a removable piston-retaining module releasably connected to the shaft for up and down reciprocating movement within the housing in response to operation of the drive mechanism, the piston-retaining module including a rack having a plurality of laterally spaced cells, each cell comprsiing top, first and second side, rear, and U-shaped bottom walls and an open front for receiving a replaceable piston module, each U-shaped bottom wall being aligned with a different cylinder port in the bototm wall of the housing, a plurality of separately removable piston modules each comprising a different one of the pistons including a rod having an upper end insertable into and removable from a different cell in the piston-retaining module through the open front thereof to align with a different cylinder port in the bottom wall of the housing, spring capturing means disposed proximate the upper end of the rod, and a piston spring disposed about the rod betwene the spring capturing means and the U-shaped bottom wall of the cell to continuously urge the upper end of the rod against the top wall of the cell with a lower end of the rod extending through the U-shaped bottom wall of the cell, and a plurality of separately removable cylinder modules each comprising a different one of the cylinders including a cylindrical member having an upper end receiving a lower end of a different rod of a different piston module within the housing to extend axially in line with a different cylinder port in the bottom wall of the housing with a lower tapered end of the cylinder extending through the cylinder port to receive a removable pipette tip.

6. The modular liquid-end assembly of claim 5 including cooperative and releasable locking means on a back wall of the housing and on each cylinder module for releasably securing each cylinder module within the housing for easy removal and replacement as desired through the openable front wall of the housing.

7. The modular liquid-end assembly of claim 6, wherein the cooperative means includes a detent extending rearwardly from each cylinder module and a plurality of laterally spaced sockets in the back wall of the housing each for receiving a different detent to releasably secure an associated cylinder module within the housing.

8. The modular liquid-end assembly of claim 5, wherein each cylinder module includes axially compressible O-ring sealing means for receiving an associated rod of an associated piston module to provide a fluid seal around the associated rod and means for axially compressing the O-ring seal means located within each cylinder module.

* * * * *